(12) United States Patent
Alchemy et al.

(10) Patent No.: US 12,239,445 B1
(45) Date of Patent: Mar. 4, 2025

(54) PINCH STRENGTH APPARATUS AND METHODS THEREOF

(71) Applicant: Alchemy Logic Systems, Inc., Santa Rosa, CA (US)

(72) Inventors: Grace Alchemy, Santa Rosa, CA (US); Sarah Alchemy, Santa Rosa, CA (US); Bruce Bolon, Roseville, MN (US); Jerry Artz, Saint Paul, MN (US); John William Alchemy, Santa Rosa, CA (US)

(73) Assignee: Alchemy Logic Systems Inc., Santa Rosa, CA (US)

( * ) Notice: Subject to any disclaimer, the term of this patent is extended or adjusted under 35 U.S.C. 154(b) by 549 days.

(21) Appl. No.: 17/673,389

(22) Filed: Feb. 16, 2022

Related U.S. Application Data

(60) Provisional application No. 63/163,355, filed on Mar. 19, 2021.

(51) Int. Cl.
*A61B 5/22* (2006.01)
*A61B 5/00* (2006.01)

(52) U.S. Cl.
CPC ............ *A61B 5/225* (2013.01); *A61B 5/0002* (2013.01); *A61B 5/68* (2013.01)

(58) Field of Classification Search
CPC .......... A61B 5/225; A61B 5/0002; A61B 5/68
See application file for complete search history.

(56) References Cited

U.S. PATENT DOCUMENTS

| | | | |
|---|---|---|---|
| 4,916,611 A | 4/1990 | Doyle, Jr. et al. | |
| 4,987,538 A | 1/1991 | Johnson et al. | |
| 5,174,154 A * | 12/1992 | Edwards | A61B 5/225 |
| | | | 600/587 |
| 5,182,705 A | 1/1993 | Barr et al. | |
| 5,367,675 A | 11/1994 | Cheng et al. | |
| 5,517,405 A | 5/1996 | McAndrew et al. | |
| 5,544,044 A | 8/1996 | Leatherman | |
| 5,613,072 A | 3/1997 | Hammond et al. | |
| 5,778,345 A | 7/1998 | McCartney | |
| 5,911,132 A | 6/1999 | Soane | |
| 6,003,007 A | 12/1999 | DiRienzo | |

(Continued)

FOREIGN PATENT DOCUMENTS

| | | |
|---|---|---|
| CA | 2707207 A1 | 6/2009 |
| WO | 2008006117 A2 | 1/2008 |

(Continued)

OTHER PUBLICATIONS

"CA DWC Releases 4th Edition of Physician's Guide to Medical Practice in CA WC", Apr. 5, 2016, workcompwire.com, 7 pages.

(Continued)

*Primary Examiner* — Jamel E Williams
(74) *Attorney, Agent, or Firm* — Haverstock & Owens, A Law Corporation

(57) ABSTRACT

An average coefficient of static friction between skin and paper is determined based on pinch-strength measurements and a corresponding maximum weight of bucket and water before slippage occurs. With the coefficient of static friction determined, a pinch-strength threshold for impairment uniquely determines the threshold for a weight of a pinch test apparatus using one or more common or household material(s), such as bucket and water. A patient using such apparatus at home can therefore put sufficient water in the bucket to reach this weight and see if they can lift the bucket or not, thereby determining whether or not impairment exists.

20 Claims, 3 Drawing Sheets

(56) References Cited

U.S. PATENT DOCUMENTS

| | | | |
|---|---|---|---|
| 6,065,000 A | 5/2000 | Jensen | |
| 6,604,080 B1 | 8/2003 | Kern | |
| 6,810,391 B1 | 10/2004 | Birkhoelzer et al. | |
| 6,865,581 B1 | 3/2005 | Cloninger, Jr. | |
| 6,954,730 B2 | 10/2005 | Lau et al. | |
| 6,957,227 B2 | 10/2005 | Fogel | |
| 7,331,721 B2 | 2/2008 | Beinat | |
| 7,401,056 B2 | 7/2008 | Kam | |
| 7,440,904 B2 | 10/2008 | Hasan et al. | |
| 7,475,020 B2 | 1/2009 | Hasan et al. | |
| 7,509,264 B2 | 3/2009 | Hasan et al. | |
| 7,630,911 B2 | 12/2009 | Kay | |
| 7,630,913 B2 | 12/2009 | Kay | |
| 7,707,046 B2 | 4/2010 | Kay | |
| 7,707,047 B2 | 4/2010 | Hasan et al. | |
| 7,778,849 B1 | 8/2010 | Hutton | |
| 7,813,944 B1 | 10/2010 | Luk | |
| 7,870,011 B2 | 1/2011 | Kay | |
| 7,904,309 B2 | 3/2011 | Malone | |
| 7,930,190 B1 | 4/2011 | Millanovich | |
| 7,949,550 B2 | 5/2011 | Kay | |
| 7,970,865 B2 | 6/2011 | DeCesare et al. | |
| 8,019,624 B2 | 9/2011 | Malone | |
| 8,041,585 B1 | 10/2011 | Binns et al. | |
| 8,065,163 B2 | 11/2011 | Morita et al. | |
| 8,069,066 B2 | 11/2011 | Stevens et al. | |
| 8,185,410 B2 | 5/2012 | Brigham | |
| 8,301,575 B2 | 10/2012 | Bonnet et al. | |
| 8,346,573 B2 | 1/2013 | Glimp et al. | |
| 8,425,524 B2 | 4/2013 | Aker et al. | |
| 8,489,413 B1 | 7/2013 | Larson et al. | |
| 8,489,424 B2 | 7/2013 | Hasan et al. | |
| 8,510,134 B1 | 8/2013 | Sweat | |
| 8,527,303 B2 | 9/2013 | Kay | |
| 8,615,409 B1 | 12/2013 | McKown | |
| 8,630,878 B1 | 1/2014 | Kravets et al. | |
| 8,725,538 B2 | 5/2014 | Kay | |
| 8,751,252 B2 | 6/2014 | Chamberlain | |
| 8,751,263 B1 | 6/2014 | Cave et al. | |
| 8,751,266 B2 | 6/2014 | Stang | |
| 8,775,216 B1 | 7/2014 | Amick et al. | |
| 8,864,663 B1 | 10/2014 | Kahn et al. | |
| 8,868,768 B2 | 10/2014 | Sokoryansky | |
| 8,888,697 B2 | 11/2014 | Bowman et al. | |
| 8,900,141 B2 | 12/2014 | Smith et al. | |
| 8,910,278 B2 | 12/2014 | Daune et al. | |
| 8,930,225 B2 | 1/2015 | Morris | |
| 8,959,027 B2 | 1/2015 | Kusens | |
| 8,954,339 B2 | 2/2015 | Schaffer | |
| 9,002,719 B2 | 4/2015 | Tofte | |
| 9,015,055 B2 | 4/2015 | Tirinato et al. | |
| 9,020,828 B2 | 4/2015 | Heidenreich | |
| 9,031,583 B2 | 5/2015 | Periera | |
| 9,229,917 B2 | 1/2016 | Larcheveque | |
| 9,710,600 B1 | 7/2017 | Dunleavy | |
| 11,461,848 B1* | 10/2022 | Alchemy | G16H 10/60 |
| 11,625,687 B1* | 4/2023 | Alchemy | G06Q 10/1053 705/321 |
| 11,848,109 B1* | 12/2023 | Alchemy | G16H 15/00 |
| 11,853,973 B1* | 12/2023 | Alchemy | G16H 40/63 |
| 11,854,700 B1* | 12/2023 | Alchemy | G16H 50/20 |
| 2001/0027331 A1 | 10/2001 | Thompson | |
| 2001/0044735 A1 | 11/2001 | Colburn | |
| 2001/0053984 A1 | 12/2001 | Joyce | |
| 2002/0069089 A1 | 6/2002 | Larkin | |
| 2002/0077849 A1 | 6/2002 | Baruch | |
| 2004/0044546 A1 | 3/2004 | Moore | |
| 2004/0144156 A1* | 7/2004 | Becker | G01L 25/00 73/1.08 |
| 2005/0060184 A1 | 3/2005 | Wahlbin | |
| 2005/0177403 A1 | 8/2005 | Johnson | |
| 2005/0256744 A1 | 11/2005 | Rohde | |
| 2006/0161456 A1 | 7/2006 | Baker | |
| 2006/0287879 A1 | 12/2006 | Malone | |
| 2007/0118406 A1 | 5/2007 | Killin | |
| 2007/0250352 A1 | 10/2007 | Tawil | |
| 2008/0046297 A1 | 2/2008 | Shafer | |
| 2008/0133297 A1 | 6/2008 | Schmotzer | |
| 2008/0154672 A1 | 6/2008 | Skedsvold | |
| 2008/0183497 A1 | 7/2008 | Soon-Shiong | |
| 2009/0099875 A1 | 4/2009 | Koenig | |
| 2010/0042435 A1 | 2/2010 | Kay | |
| 2010/0106520 A1 | 4/2010 | Kay | |
| 2010/0106526 A1 | 4/2010 | Kay | |
| 2010/0114609 A1 | 5/2010 | Duffy, Jr. | |
| 2010/0217624 A1 | 8/2010 | Kay | |
| 2010/0240963 A1 | 9/2010 | Brighman | |
| 2011/0077980 A1 | 3/2011 | Kay | |
| 2011/0077981 A1 | 3/2011 | Kay | |
| 2011/0161115 A1 | 6/2011 | Hampton | |
| 2011/0257919 A1 | 10/2011 | Reiner | |
| 2011/0257993 A1 | 10/2011 | Shahani | |
| 2011/0313785 A1 | 12/2011 | Lash | |
| 2011/0313912 A1 | 12/2011 | Teutsch | |
| 2012/0102026 A1 | 4/2012 | Fortune | |
| 2012/0130751 A1 | 5/2012 | McHugh | |
| 2012/0232924 A1 | 9/2012 | Bingham | |
| 2012/0245973 A1 | 9/2012 | Pandya | |
| 2012/0278095 A1 | 11/2012 | Homchowhury | |
| 2012/0280931 A1 | 11/2012 | Stephanick | |
| 2012/0284052 A1 | 11/2012 | Saukas | |
| 2013/0024214 A1 | 1/2013 | Shoen | |
| 2013/0132122 A1 | 5/2013 | Walsh | |
| 2014/0058763 A1 | 2/2014 | Zizzamia | |
| 2014/0073486 A1 | 3/2014 | Ahmed | |
| 2014/0136216 A1 | 5/2014 | Beebe | |
| 2014/0172439 A1 | 6/2014 | Conway | |
| 2014/0201213 A1 | 7/2014 | Jackson | |
| 2014/0249850 A1 | 9/2014 | Woodson | |
| 2014/0278479 A1 | 9/2014 | Wang | |
| 2014/0278830 A1 | 9/2014 | Gagne | |
| 2014/0303993 A1 | 10/2014 | Florian | |
| 2014/0379364 A1 | 12/2014 | Liu et al. | |
| 2015/0019234 A1 | 1/2015 | Cooper | |
| 2015/0221057 A1 | 8/2015 | Raheja | |
| 2015/0235334 A1 | 8/2015 | Wang | |
| 2015/0242585 A1 | 8/2015 | Spiegel | |
| 2015/0278462 A1 | 10/2015 | Smoley | |
| 2015/0286792 A1 | 10/2015 | Gardner | |
| 2015/0324523 A1 | 11/2015 | Parthasarathy | |
| 2016/0063197 A1 | 3/2016 | Kumetz | |
| 2016/0110334 A1* | 4/2016 | Yu | G06F 11/0769 715/223 |
| 2016/0125544 A1 | 5/2016 | Edwards | |
| 2016/0259499 A1 | 9/2016 | Kocienda | |
| 2016/0283676 A1 | 9/2016 | Lyon | |
| 2016/0292371 A1 | 10/2016 | Alhimin | |
| 2016/0342745 A1 | 11/2016 | Gupta | |
| 2017/0140489 A1 | 5/2017 | Ziobro | |
| 2017/0177810 A1 | 6/2017 | Fulton | |
| 2017/0228517 A1 | 8/2017 | Saliman | |
| 2017/0255754 A1 | 9/2017 | Allen | |
| 2017/0286389 A1* | 10/2017 | Ceneviva | G06F 40/106 |
| 2017/0316424 A1 | 11/2017 | Messana | |
| 2018/0025334 A1 | 1/2018 | Pourfallah | |
| 2019/0065686 A1 | 2/2019 | Crane | |
| 2019/0159747 A1 | 5/2019 | Zanca | |
| 2020/0126645 A1 | 4/2020 | Robbins | |
| 2020/0279622 A1 | 9/2020 | Heywood | |
| 2020/0286600 A1* | 9/2020 | De Brouwer | G16H 50/20 |
| 2022/0391993 A1* | 12/2022 | Alchemy | G06Q 40/08 |
| 2023/0196297 A1* | 6/2023 | Alchemy | G06Q 10/1053 705/321 |

FOREIGN PATENT DOCUMENTS

| | | |
|---|---|---|
| WO | 2016061340 A1 | 4/2016 |
| WO | 2018224449317 A1 | 12/2018 |

OTHER PUBLICATIONS

Hakkinen, Arja, et al. "Muscle strength, pain, and disease activity explain individual subdimensions of the Health Assessment Questionaire

(56) References Cited

OTHER PUBLICATIONS disability index, especially in women with rheumatoid arthritis". Annals of the rheumatic diseases 65.1 (2006): 30-34. (Year: 2006).
In B. Pffafenberger, Webster's new World & Trade; Computer Dictionary (10th ed). Houghton Mifflin Harcourt, Credo reference:https://search.credorreference.com/content/entry/webster.com/database (year 2003).
American College of Occupational and Environmental Medicine, Occupational Medicine Practice Guidelines, 2004, Second Edition, OEM Press, Beverly Farms, MA.
CA Medical Treatment Utilization Schedule, Proposed Chronic Pain Medical Treatment Guidelines, Jun. 2008, 83 pages.
Park, Y., & Butler, R. J. (2000). Permanent Partial Disability Awards and Wage Loss, Journal of Risk and Insurance, 67(3), 331, retrieved from https://dialog.proquest.com/professional/docview/769439682?accountid=142257 (Year: 2000).
Philosophy, Purpose, and Appropriate Use of the Guides, Chapter 1, American Medical Association, 618 pages.
State of California Department of Industrial Relations Division of Workers Compensation, Physicians Guide to Medical Practice in the California Workers Compensation System, Fourth Edition, 2016, 137 pages.
Cocchiarella, Linda and Andersson, Gunnar B.J., Guides to the Evaluation of Permanent Impairment, 2001, Fifth Edition, American Medical Association.
Rondinelli, Robert D., Guides to the Evaluation of Permanent Impairment, 2008 Sixth Edition, American Medical Association.
Ammendolia C. Cassidy D., Steensta I, et al. Designing a Workplace Return-to Work Program for Occupational Low Back Pain: an intervention mapping approach. BMC Musculoskelet Disord. 2009;10:65. Published Jun. 9, 2009. doi: 10.1186/1471-2474-10-65 (Year; 2009). 10 pages.
Wasiak, Radoslaw, et al. "Measuring Return to Work." Journal of Occupational Rehabilitation 17.4 (2007): 766-781. (Year: 2007). 16 pages.
"A Comparison of Two Methods of Measuring Static Coefficient of Friction at Low Normal Forces": A Pilot Study, Na Jin Seo et al., Ergonomics 2009, 1 Page.
University Physics Seventh Edition, Francis Sears et al., pp. 92-96, Addison-Wesley Publishing Company.
"Characterization of Skin Friction Coefficient and Relationship to Stratum Corneum Hydration in a Normal Chinese Population", Y. H. Zhu et al., pp. 81-86.
"Test of Grip and Pinch Strengths of 111 Healthy University Students in Fujian Province", Jiang Zheng et al., Journal of Clinical Rehabilitative Tissue Engineering Research , vol. 14, No. 50, pp. 9452-9456.
Baseline Pinch Gauge-Pro Healthcare Products.com., 2 Pages.
"Subacromial Space Definition", Sports-Health, 1 Page.
"The Strength-Dexterity Test as a Measure of Dynamic Pinch Performance", Journal of Biomechanics 2003, pp. 265-270.

"Coefficient of Friction: Tribological Studies in Man—An Overview", Raja K. Sivamini et al., Skin Research and Technology 2003, pp. 227-234.
"Grip Surface Affects Maximum Pinch Force", Na Jin Seo et al., vol. 53, No. 6, Dec. 2011, pp. 740-748.
"Friction Dynamics on Human Skin Surfaces", Yashimune Nonomura and Haruka Ouchi, Journal of Oleo Science, Copyright 2020 by Japan Oil Chemists Society, pp. 461-465.
"A Quantitative Shoulder Strength Testing Method for in-Person and Telemedicine Examinations", Mari Johnson et al., Journal of Clinical Cases and Reports, Case Report , vol. 4, ISS S6.
"Hand Grip Strength Variability During Serial Testing as an Entropic Biomarker of Aging": Poincare Plot Analysis BMC Geriatrics, Elena Loana Iconaru and Constantin Ciucurel,Dec. 2020, 12 Pages.
"Towards a Comprehensive Functional Capacity Evaluation for Hand Function," www.elsevier.com/locate/apergo, N. Hollak et al., Jan. 17, 2013, pp. 1-7.
Telemedicine: "Is it a Tool for Orthopedics"?, Current Reviews in Musculoskeletal Medicine, Oct. 23, 2020, pp. 797-799.
"Handgrip Strength Measured by a Dynamometer Connected to a Smartphone": a new applied health technology solution for the self assessment of Francisco Espinoza et al. pp. 897-900.
"Assessment of Hand-Grip and Key-Pinch Strength at Three Arm Positions Among Healthy College Students: Dominant versus Non-Dominant Hand", Journal of Talibah University Medical, Tarek M. El-Gohary, Ph.D., Jun. 25, 2019, pp. 566-571.
"Cost Effectiveness of Telemedicine in Remote Orthopedic Consultations: Randomized Controlled Trial", Journal of Medical Internet Research Astrid Buvik et al., 2019, vol. 21, Issue 2, 2 Pages.
"Friction Between Hand and Handle. Effects of Oil and Lard on Textured and Non Textured Surfaces; Perception of Discomfort", Applied Ergonomics, Olle Bobjer et al., vol. 24, Issue 3, Jun. 1993, pp. 190-202.
"Prediction of Grip and Key Pinch Strength in 978 Healthy Subjects",www.biomedcentral.com., Felix Angst et al., 2010, 6 Pages.
"A Novel Method of Monofilament Force Testing for Nerve Sensory Loss in Telemedicine", John Alchemy et al., Copyright 2019 Alchemy et al., vol. 7, Issue 1, 6 Pages.
AMA Guides 5th Edition, Chapter 1 Philosophy, Purpose, and Appropriate Use of the Guides, 618 Pages, Reference purposes see pp. 507-509.
"Normative data for hand grip strength and key pinch strength, stratified by age and gender for a multiethnic Asian population", Lam et al., pp. 578-584, 2016.
"Influences of gender, hand dominance, and anthropometric characteristics on different types of pinch strength: a partial least squares (PLS) approach", Maleki-Ghahfarokhi et al., pp. 9-16, 2019.
"Normative values for grip and pinch strength for 6-19-Year-Olds", McQuiddy et al., pp. 1627-1633, 2015.
"The influence of gender, grasp type, pinch width and wrist position on sustained pinch strength", Dempsey, P.G. et al., pp. 259-273, 1996.

* cited by examiner

PINCH STRENGTH APPARATUS AND METHODS THEREOF

RELATED APPLICATIONS

This application claims the benefit under 35 U.S.C. § 119(e) of provisional application 63/163,355, filed Mar. 19, 2021, the entire contents of which is hereby incorporated by reference for all purposes as if fully set forth herein.

TECHNICAL FIELD

The present invention is generally directed to telemedicine. More specifically, the present invention is directed to systems and methods of testing pinch test.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Neuromuscular hand strength evaluation is challenging under the best clinical circumstances. With the rapidly growing importance of telemedicine and video-assisted medical examination, objective assessment of the hand neuromuscular function persists as a difficult challenge. The COVID-19 pandemic ushered in a rapid transition to online medical visits. The increased volume of virtual patient visits pushed physicians to adapt physical examinations into a suitable format for online evaluation. The hand motor strength exam (pinch and grip) typically relies on expensive standardized medical-office measurement devices, such as a pinch dynamometer. The pinch test is a major element of the hand neurovascular exam that practitioners rely on for valuing injury impairments and functional loss involving the elbows, wrists, hands, fingers, and thumbs. Outside the clinical setting, telemedicine providers require a reproducible method of standardizing pinch-strength testing. There is currently no such method for remote measurement.

Accordingly, there is a need for techniques to determine a minimum pinch-strength of an individual outside the clinical setting and that provide results consistent with those obtained in the office, thereby providing extremely valuable alternatives.

SUMMARY

The present invention is directed to an apparatus and methods of determining a minimum pinch-strength threshold for an individual using common or household item(s). A standard sheet of copy paper is folded and used to support the handle of a 2.5-gallon container, such as a bucket, containing a variable amount of water. The paper is pinched between the thumb and index finger, and the bucket of water is lifted. An average coefficient of static friction between skin and paper is determined using pinch-strength measurements and a corresponding maximum weight of bucket and water before slippage occurs. Determining the coefficient of static friction between skin and paper allows for remote evaluation of pinch strength using a folded sheet of paper. For example, a pinch-strength threshold for impairment (e.g., 4.9 kg for women and 7.5 kg for men) uniquely determines the threshold for a weight of a pinch test apparatus using one or more common or household item(s), such as bucket and water. A patient using such apparatus at home can therefore put sufficient water in the bucket to reach this weight and see if they can lift the bucket or not, thereby determining whether or not impairment exists.

In one aspect, a pinch test apparatus comprises a collection of one or more household items coupled together. The collection of one or more household items has an opening. In an embodiment, wherein the collection of one or more household items includes a bucket of water. The pinch test apparatus also comprises a piece of paper that is folded longitudinally into a strip. In an embodiment, the piece of paper folded is longitudinally three times to form an eight-ply strip. The strip is looped through the opening and ends of the strip are aligned. In an embodiment, thickness of the strip is 0.2 cm. In an embodiment, the pinch test apparatus also includes a clothespin coupled with the strip. The clothespin holds the strip in place and ensures that the paper surfaces in contact with thumb and index finger are parallel to each other. In an embodiment, the weight of the pinch test apparatus is approximately 2.84 kg (for women) or is approximately 4.35 kg (for men).

In another aspect, a method of determining a coefficient of static friction between skin and paper comprises assembling a pinch strength apparatus. In an embodiment, the pinch strength apparatus comprises a collection of one or more household items coupled together. The collection of one or more household items has an opening. In an embodiment, the collection of one or more household items includes a bucket of water. The pinch strength apparatus further comprises a piece of paper folded longitudinally into a strip. In an embodiment, a thickness of the strip is 0.2 cm. The pinch strength apparatus is assembled by looping the strip through the opening. In an embodiment, the pinch strength apparatus further comprises a clothespin. The clothespin is coupled horizontally to the strip and is configured as a guide for positioning fingers in the hand position.

The method comprises determining a baseline pinch strength. In an embodiment, the baseline pinch strength is determined by using a pinch dynamometer.

The method comprises determining a threshold weight of the pinch strength apparatus. In an embodiment, the threshold weight comprises using a hand position in a key pinch to grip the strip. The key pinch involves a volar pad of a thumb on one side of an object (e.g., strip, pinch dynamometer) and a radial side of a distal phalanx of an index finger on an opposite side of the object.

The method comprises lifting the pinch strength apparatus from the ground with elbow at full extension, returning the pinch strength apparatus to the ground, and assessing whether there is slippage of the paper between fingers. The method comprises, in response to assessing that there is no slippage, increasing mass of the pinch test apparatus and repeating using the hand position in the key pinch, lifting the pinch strength apparatus, returning the pinch strength apparatus, and assessing whether there is slippage. The method comprises, in response to assessing that there is slippage, decreasing the mass of the pinch test apparatus and repeating using the hand position in the key pinch, lifting the pinch strength apparatus, returning the pinch strength apparatus, and assessing whether there is slippage.

The method comprises, based on the baseline pinch strength and the weight of the pinch strength apparatus, determining a value of a coefficient of static friction between skin and paper.

In yet another aspect, a method of testing a pinch strength comprises assembling a pinch strength apparatus. In an embodiment, the pinch strength apparatus comprises a collection of one or more household items coupled together. The collection of one or more household items has an opening. In an embodiment, the collection one or more household items includes a bucket of water. The pinch strength apparatus further comprises a piece of paper folded longitudinally three times into a strip. In an embodiment, a thickness of the strip is 0.2 cm. The pinch strength apparatus is assembled by looping the strip through the opening. In an embodiment, the pinch strength apparatus further comprises a clothespin. The clothespin is coupled horizontally to the strip and is configured as a guide for positioning fingers in the hand position.

The method comprises using a hand position in a key pinch to grip the strip. The key pinch involves a volar pad of a thumb on one side of an object (e.g., strip, pinch dynamometer) and a radial side of a distal phalanx of an index finger on an opposite side of the object.

The method comprises lifting the pinch strength apparatus from the ground. In an embodiment, assembling, using and lifting are supervised via telemedicine.

In an embodiment, the weight of the pinch test apparatus is approximately 2.84 kg (for women) or is approximately 4.35 kg (for men). In an embodiment, the method further comprises assessing whether there is slippage of the paper between fingers when the pinch strength apparatus is lifted from the ground and determining whether an impairment exists based on at least the assessment.

In an embodiment, the method further comprises determining a weight of the pinch test apparatus and, based on the weight of the pinch test apparatus and a coefficient of static friction between skin and paper, determining pinch strength determining the pinch strength comprises.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

Figure 1:
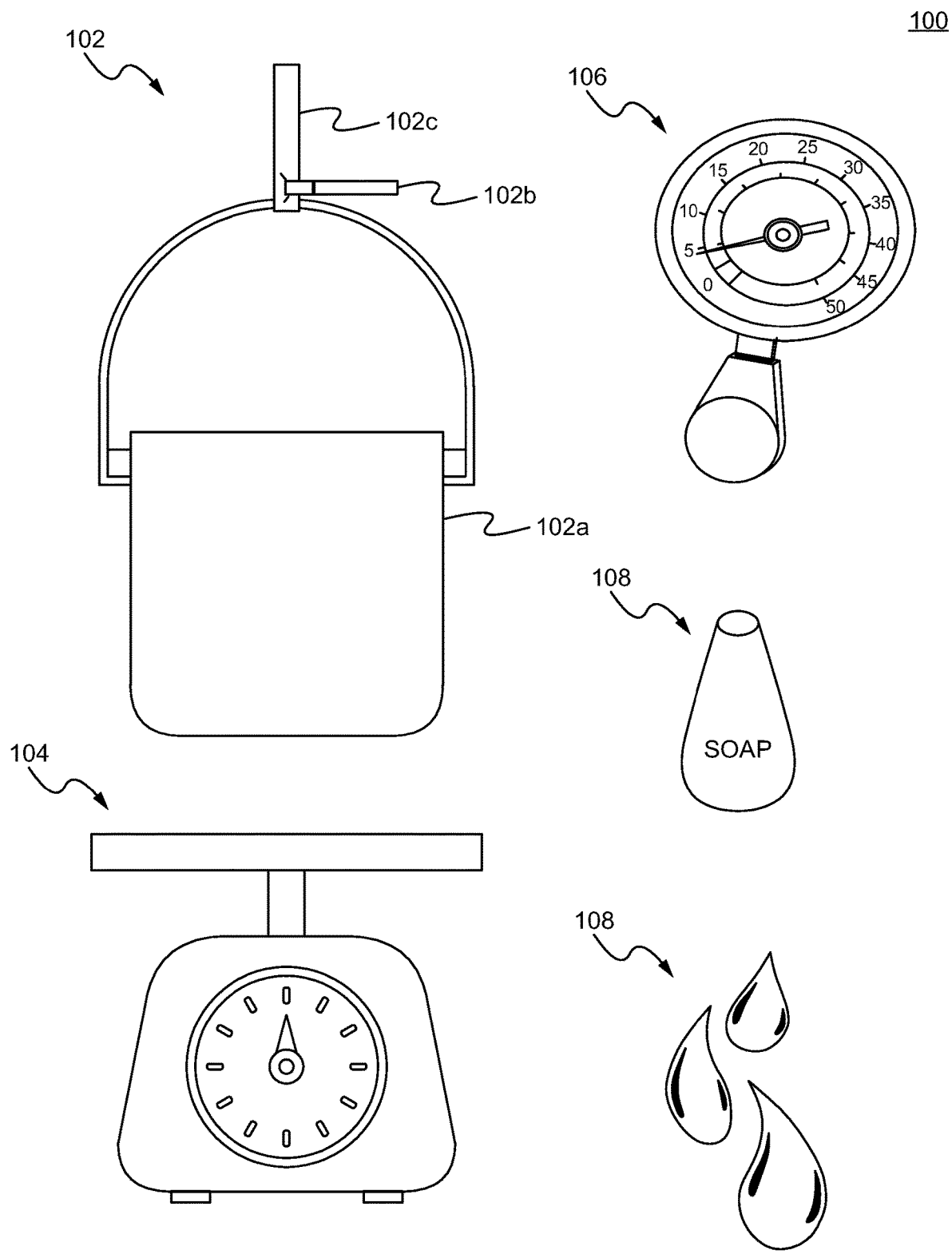
FIG. 1 illustrates a system for determining the coefficient of static friction between skin and paper in accordance with some embodiments.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein in sections according to the following outline:
1.0 GENERAL OVERVIEW
2.0 PINCH STRENGTH OVERVIEW
3.0 COEFFICIENT OF STATIC FRICTION
  3.1 SYSTEM SETUP
  3.2 ENVIRONMENTAL FORCES
  3.3 DETERMINING THE COEFFICIENT OF STATIC FRICTION
4.0 REMOTE EVALUATION OF PINCH STRENGTH
5.0 OTHER ASPECTS OF DISCLOSURE

1.0 GENERAL OVERVIEW

Techniques described herein determine the coefficient of static friction between paper and human skin in order to create a practical application to measure pinch strengths of patients. Coefficient of static friction values for skin on paper are not found in standard tables (e.g., *Handbook of Chemistry and Physics*), nor are the values published in the *AMA Guides to the Evaluation of Permanent Impairment, 5th Edition* (hereafter, the "*AMA Guides*") (Andersson & Cocchiarella, 2006). With the coefficient of static friction determined, the pinch-strength threshold for impairment (corresponding to 4.9 kg for women and 7.5 kg for men) uniquely determines the threshold for a weight of a household material(s), such as bucket and water. A patient using such apparatus at home can therefore put sufficient water in the bucket to reach this weight and see if they can lift the bucket or not, thereby determining whether or not impairment exists. The results may serve as the foundation for establishing a baseline protocol for remote examination of quantitative functional pinch-testing.

Other embodiments, aspects, and features will become apparent from the reminder of the disclosure as a whole.

2.0 PINCH STRENGTH OVERVIEW

Understanding impairment is challenging in a clinical setting for even the most experienced practitioner. Providing accurate and substantive diagnostic evaluations generally requires a thorough examination across a range of tasks and the use of careful and reproducible measurements. This combination of expectations often means that impairment ratings are available only to patients with access (logistically and financially) to experienced diagnosticians in specialized facilities. Because impairment can result from work-related injuries, personal injury, and progressive conditions, the incentive for pursuing a diagnosis and seeking treatment varies widely. Efforts to make such examinations more convenient and accessible to more patients, yet still provide reliable results, could lead to dramatically improved care and quality of life across a wide sector of the population.

Discussion herein focuses on the pinch strength needed to accomplish activities of daily living (ADLs) and a new ways of assessing this important measure remotely, such as in the home. Measurement of pinch strength traditionally requires access to a dynamometer, a specific device used to test neuromuscular capacity. Alternatives that use materials and techniques readily available can overcome the challenge of the remote examination without having this dynamometer. Techniques described herein propose an effective, reliable method for testing the functionality of the hand in such a way that people can perform test remotely. This method requires no specialized medical equipment nor purchase of medical equipment nor does a clinic need to mail out any medical equipment to the patient.

Techniques described herein allow a telemedicine practitioner to answer questions related to the threshold pinch strength of the patient. Those answers are based on the patient's experience following instructions for manipulating readily available household items. The practitioner, then, can evaluate the patient in relation to thresholds established in the *AMA Guides*. According to the *AMA Guides*, these thresholds require a 4.9-kg minimum pinch strength for female patients and a 7.5-kg minimum pinch strength for male patients.

Direct measurement of these forces is possible in the clinic with a classic pinch gauge. The gauge can be helpful in detecting the specific pinch strength singly or across a series of repetitions of the test. Its usefulness in demonstrating impairment extends to the generation of measurements that fall below the threshold. When a gauge is not available, the full range of measurements may be cumbersome to collect. However, for evaluating the strength necessary to achieve the threshold, a gauge is not necessary. In the absence of a gauge, a method for recording pinch strength above or below the threshold may be demonstrated accurately and reliably to AMA Guides.

The adoption of telemedicine raises concerns about the efficacy of clinical practice and introduces new financial pressure on the economic model of health care clinics. A recent study of these concerns and pressures in orthopedic care concluded that under circumstances where the number of patients seeking care meets a certain threshold, clear benefits to the population emerge. These circumstances also depend on the distance that patients need to travel and the kind of care, diagnosis, or treatment being sought. Offering video-assisted consultations without the patient needing to leave home raises even greater concerns about efficacy, but these consultations may reduce reliance on regional clinics that are better provisioned for direct care.

A literature review of telemedicine in orthopedics concluded that a growing number of publications illustrate the effectiveness of telemedicine. Remote follow-up in postoperative cases including fractures as well as fracture diagnosis has consistently yielded good results, both in patient satisfaction and quality of care. Standardizing orthopedic examination is emerging as the next frontier in telemedicine for musculoskeletal conditions.

Telemedicine may not be the only application for these techniques, when a fast, reliable determination of strength is needed to complete an evaluation. Even in a clinical setting, a pinch gauge may be misplaced or malfunctioning at the time of an examination, leading to incomplete or inaccurate reporting of this measure of strength for ADLs.

In clinical experience of one of the inventors who has expertise in completing evaluations of the hand, pinch strength loss measurements tend to be "higher value" impairment ratings, meaning the Whole Person Impairment (WPI) values may be higher than those of joint range of motion or peripheral nerve loss. Hand functions including pinch strength involve at least 14 ADLs, ranging from non-specialized hand activities and self-care to communication, driving, and sleep across a wide range of actions. Previous research demonstrates that telemedicine opens new opportunities for clinicians to evaluate more patients for strength and range of motion function that can lead to better care and more complete access to compensation for all stakeholders.

Techniques discussed herein provide a single threshold measure of whether a patient can achieve the pinch strength recognized to accomplish ADLs, and not to provide incremental quantitative measures of the strength as it varies over time.

Pinch strength herein is distinguished from the wider range of activities classified with grip strength. In general, unsupported grip includes the capacity and strength of finger, hand, and wrist muscles and the associated physiology.

3.0 COEFFICIENT OF STATIC FRICTION

As explained herein, determining the presence of the normal pinch strength threshold requires no specialized device and no visit to the clinic. Using household materials commonly available, and supervision via telemedicine, a patient can follow the steps of the procedure presented herein. The procedure provides a threshold weight to test the strength of the pinch between a thumb (volar pad) and an index finger (radial side of the distal phalanx) of the patient. In evaluating hand function, the full battery of tests can complicate measures of particular functions, such as pinch strength. The strength of the pinch between the thumb and the index finger involves comparing the patient's ability to lift a known weight by pinching a folded sheet of paper wrapped around a household material(s), such as the handle of a bucket of water.

Remote evaluation of pinch strength using a folded sheet of paper depends on knowing the coefficient of static friction, $\mu_s$, between skin and paper. However, this coefficient of static friction is not disclosed in any standard tables or the AMA Guides. The following describes a technique for determining the coefficient of static friction between skin and paper.

3.1 System Setup

FIG. 1 illustrates a system 100 for determining the coefficient of static friction between skin and paper in accordance with some embodiments. The system 100 includes components, such as a pinch strength apparatus 102, a pinch dynamometer 104 (e.g., Baseline 12-0026 pinch gauge), a scale 106 (e.g., ACCUTECK series W-8250), liquid hand soap 108, and water 110. The pinch dynamometer 104 and the scale 106 are factory calibrated. As further discussed herein, pinch strength, as measured by the pinch dynamometer 104, is used to determine the coefficient of static friction between skin and paper.

In an embodiment, the pinch strength apparatus 102 includes a handled bucket 102a, a clothespin 102b, and a piece of paper 102c. The bucket 102 is a 2.5-gallon bucket. The paper 102c is an 8.5×11 inches, multipurpose copy printer paper and is folded three times longitudinally into an eight-ply strip. When determining the coefficient of static friction between skin and paper, the paper 102c is wrapped centrally and evenly around the middle of the handle of the bucket 102a (ends of the strip are aligned). The strip is held in place with the clothespin 102b. The assembly of the bucket 102a, the clothespin 102b, and the paper 102c is illustrated in FIG. 2.

3.2 Environmental Forces

Figure 2:
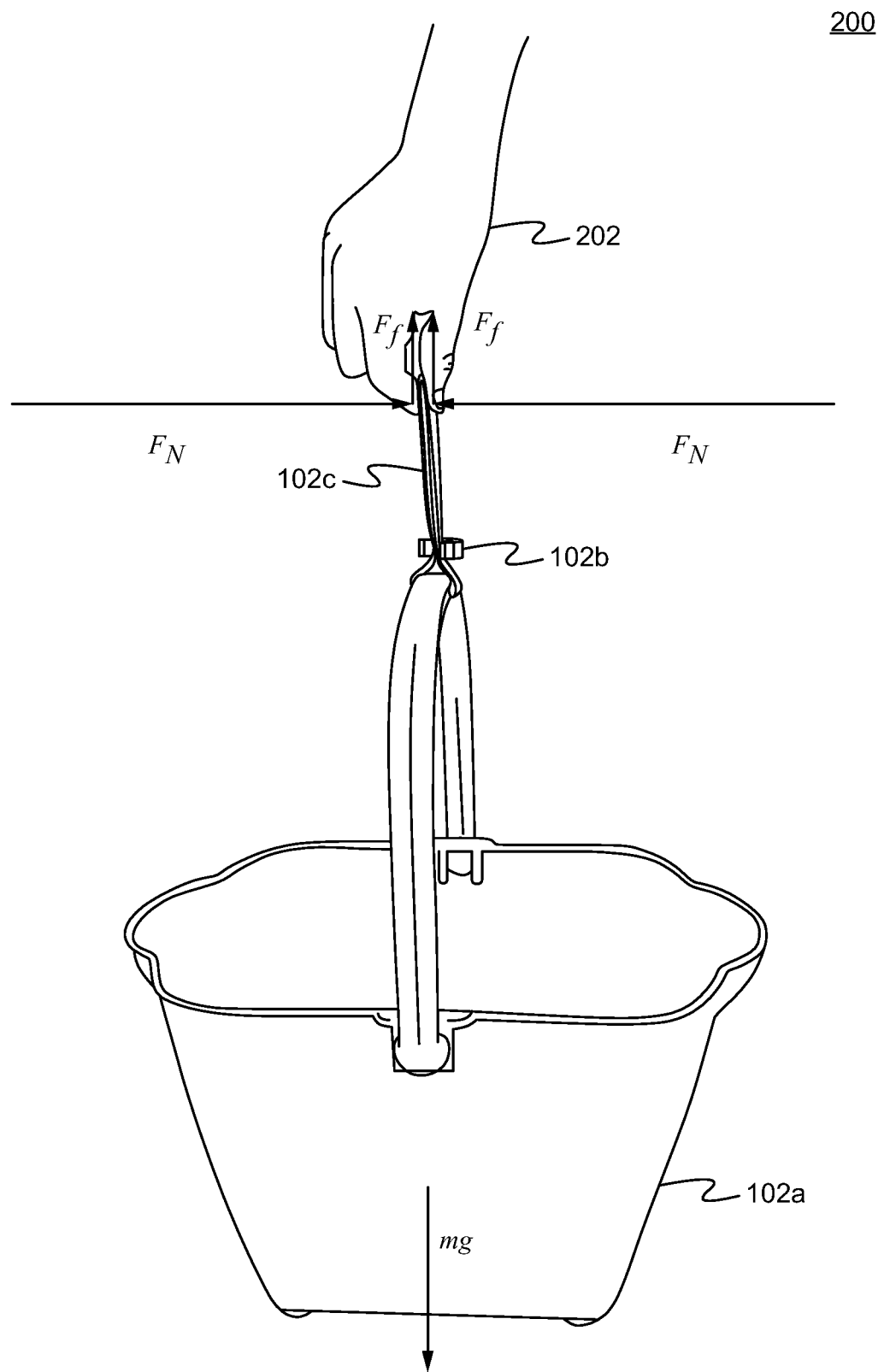
FIG. 2 illustrates a diagram showing forces acting on a bucket of water.

FIG. 2 illustrates a diagram 200 showing forces acting on the bucket 102a of water (including negligible contributions from the clothespin 102b and the paper 102c). All measurements correspond to the case when water has been added to the bucket 102a to the point that a person can just barely prevent the paper 102c from slipping. The clothespin 102b acts as a guide and ensures that the paper surfaces in contact with the thumb and index finger are parallel to each other. It also ensures that the normal forces, $F_N$, applied on each side are horizontal, and the static frictional forces, $F_f$, are vertical. It is noted that the system is in equilibrium (i.e., not accelerating). Because of this, symmetry requires that the normal forces are equal in magnitude, and therefore, so are the frictional forces. This symmetry is accounted for by labeling the magnitudes of these forces identically on each side of the force diagram of FIG. 2. It is noted that an intentional vertical orientation of the gripped surfaces eliminated consideration of the variation in coefficient of static friction resulting from angled surfaces.

The static frictional force (when slippage is just about to occur) is related to the normal force by the equation $F_f = \mu_s F_N$, and mg is the weight of the bucket of water. Since the system is not accelerating, the net force in any direction must be zero, by Newton's $2^{nd}$ Law ($\Sigma \vec{F} = m\vec{a}$). Using this force diagram and labeling upward the +y-direction yields:

$$\Sigma F_y = F_f + F_f - mg = ma_y$$

or $$\Sigma F_y = 2\mu_s F_N - mg = 0,$$

which gives:

$$\mu_S = \frac{mg}{2F_N}.$$

$F_N$ is assumed to be equivalent to the maximum measurement obtained separately utilizing the pinch dynamometer 108. The coefficient of static friction is proportional to the ratio of the weight of the bucket to the pinch strength. Hence, a lower pinch strength $F_N$ will result in a lower weight of the bucket that can be raised and will still result in the same coefficient of static friction for the individual. This setup is specifically designed so that the way in which the person pinches the paper closely mimics the way in which the pinch dynamometer 108 is used.

3.3 Determining the Coefficient of Static Friction

In an embodiment, through multiple trials, an individual can determine his or her individual pinch strength using the pinch dynamometer 104. This pinch strength measurement can then be used along with the maximum weight of bucket 102a of water that could be supported to determine the coefficient of static friction between skin and paper.

Through a series of tests, each consisting of multiple trials, at least one participant determines his or her individual pinch strength using the pinch dynamometer 104. This pinch strength measurement is then used along with the maximum weight of bucket 102a of water that could be supported to determine the coefficient of static friction between skin and paper.

Figure 3:
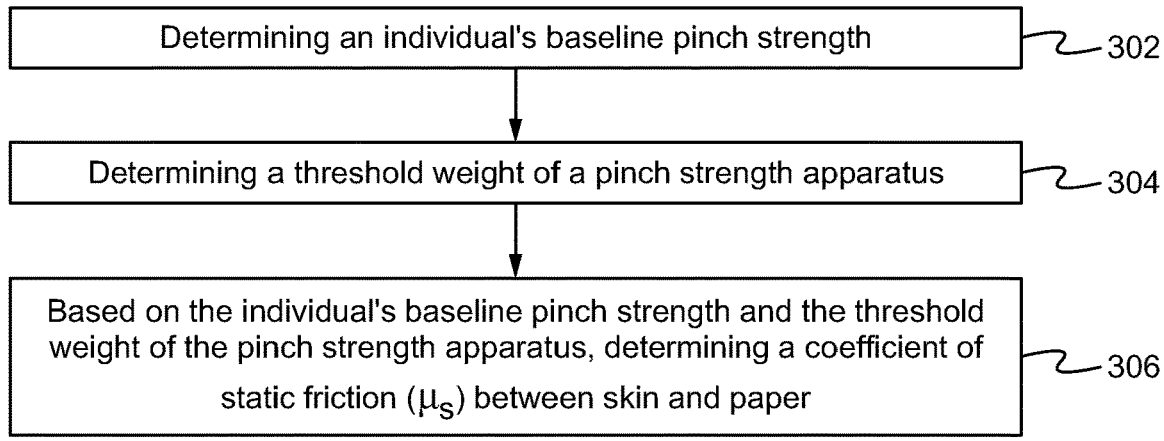
FIG. 3 illustrates a method of determining the coefficient of static friction between skin and paper in accordance with some embodiments.

FIG. 3 illustrates a method 300 of determining the coefficient of static friction between skin and paper in accordance with some embodiments. The method 300 is referred to herein as the "pinch-bucket method."

At step 302, an individual's baseline pinch strength is determined. A series of measurements of the pinch strength for each hand, dominant and non-dominant, is recorded using a key pinch on the pinch dynamometer 104. The key pinch involves the volar pad of the thumb on the dial side of the pinch dynamometer 104 and the radial side of the distal phalanx of the index finger on the underside. It is noted that only the thumb and the index finger participate in the generation of the force, excluding the remaining fingers from participation. It is critical to isolate the pinch mechanics to the thumb and index finger action only, removing any confounding contribution of the other digits. A dynamometer reading is taken each time before the bucket 102a is lifted. This reading, together with the mass of the bucket 102a and water constitute a single data point, as shown in Table 1, which is then used to calculate a corresponding coefficient of static friction.

TABLE 1

| Name/ Dominant Hand | Right Hand | | | Left Hand | | |
|---|---|---|---|---|---|---|
| Date | Dynamometer Classic Pinch $F_N$ (kg) | Bucket Mass (Kg) | $\mu_s$ | Dynamometer Classic Pinch $F_N$ (kg) | Bucket Mass (Kg) | $\mu_s$ |

At step 304, a threshold weight of the pinch strength apparatus 102 is determined. In an embodiment, the hand skin surfaces can be cleaned using a drop of liquid hand soap 108 (e.g., approximately five millimeters in diameter), washed for 15 seconds, and air dried to reduce surface skin contaminants.

A volume of approximately three kilograms of water (or some other amount such as two kilograms of water) can be placed in the bucket 102a as a starting mass. A preliminary test gripping the pinch strength apparatus 102 and lifting the bucket 102a can provide assurance that the starting weight is reasonable. The paper 102 is folded longitudinally three times to form an eight-ply strip which is looped through the handle of the bucket 102a containing water.

The individual attempts to lift the bucket from the ground with the arm approximately vertical (with the elbow at full extension) while reproducing the hand position used in the key pinch (step 302). For each weight, the individual grips an unused surface of the paper 102c and lifts the apparatus bucket 102 in a manner consistent across all trials, without jerking upward or changing the position of the arm or hand. If no slippage occurs, the bucket 102a is returned to the floor, more water is added, and an attempt at lifting is repeated.

Herein, the threshold weight is defined as the minimum weight to result in slippage of the paper 102c between the individual's fingers while the maximum pinch strength is maintained. Water is added to the bucket 102a in measured increments (e.g., approximately 0.05 kg, slightly less than a quarter cup).

The total mass of the pinch strength apparatus 102a is measured for each amount. If slippage occurred, the individual can take a one-minute break and repeat the trial with the same mass to minimize the effect of hand-pinch fatigue.

To further confirm the threshold weight (when slippage occurred), the mass of the pinch strength apparatus 102 can be decreased by the same amount previously increased (e.g., approximately 0.05 kg), and another trial can be performed. Once the threshold is reached, the combined mass of the bucket 102a, the clothespin 102b, water 110, and the paper 102c is determined using the scale 106. The individual can rest for at least five minutes between trials to reduce the effects of fatigue.

The above steps can be repeated for both the dominant and non-dominant hand for a total of 10 trials (five right and five left). The trials can be alternated between right and left hands to mitigate fatigue that might otherwise impact the data.

At step 306, based on the individual's baseline pinch strength determined at step 302 and the threshold weight of the pinch strength apparatus determined at step 304, the coefficient of static friction ($\mu_s$) between skin and paper is determined according the formula discussed above ($\mu_s = (mg)/(2F_N)$).

The method 300 may be repeated numerous times (e.g., on a large number of participants) to provide a more accurate determination of the coefficient of static friction between skin and paper. The method 300 can be repeated numerous times to find an average coefficient of static friction between skin and paper.

For example, in a study conducted by the inventors, four individual participants were involved to determine the average coefficient of static friction between skin and paper. Each was determined to be free of dermatological disease that might affect skin friction in the area under examination. For reporting purposes, each participant is identified by letter: A, B, C, or D. Participant A is a right hand dominant, 19-year-old female. Participant B is a right hand dominant, 19-year-old male. Participant C is a right hand dominant, 20-year-old female. Participant D is a left hand dominant, 52-year-old male.

The pinch-bucket method described above was used by all participants for data collection. A total of 100 data points were collected for each participant (a data point in this experiment consisted of a threshold bucket mass measurement and corresponding pinch dynamometer measurement). Of these, 50 data points were collected for the right hand and 50 for the left hand. A summary of the experimental data is reported in the following Tables 2-4.

The average of individual dynamometer pinch strengths for both female and male subjects are listed in Tables 2 and 3.

TABLE 2

SUMMARY OF AVERAGE PINCH
EQUIVALENT FORCE (KG) DATA
5 KG PINCH IS NORMAL FOR FEMALES

| | Dominant | | | Non-Dominant | | |
|---|---|---|---|---|---|---|
| Participant | Pinch (kg) | STDEV (kg) | % | Pinch (kg) | STDEV (kg) | % |
| A | 5.55 | 0.42 | 8% | 5.69 | 0.45 | 8% |
| C | 6.82 | 0.58 | 8% | 7.69 | 1.20 | 16% |
| Average | 6.18 | | | 6.69 | | |
| STDEV | 0.90 | | | 1.41 | | |
| % | 15% | | | 21% | | |

TABLE 3

SUMMARY OF AVERAGE PINCH
EQUIVALENT FORCE (KG) DATA
5 KG PINCH IS NORMAL FOR MALES

| | Dominant | | | Non-Dominant | | |
|---|---|---|---|---|---|---|
| Participant | Pinch (kg) | STDEV (kg) | % | Pinch (kg) | STDEV (kg) | % |
| B | 7.00 | 0.54 | 8% | 6.49 | 0.55 | 9% |
| D | 7.50 | 0.60 | 8% | 8.35 | 0.72 | 9% |
| Average | 7.25 | | | 7.42 | | |
| STDEV | 0.35 | | | 1.31 | | |
| % | 5% | | | 18% | | |

The average coefficient of static friction of human skin on copy paper was determined in this study to be 0.29 in Table 4.

TABLE 4

SUMMARY OF $\mu_s$ DATA

| | Dominant | | | Non-Dominant | | |
|---|---|---|---|---|---|---|
| Participant | $\mu_s$ | STDEV | % | $\mu_s$ | STDEV | % |
| A | 0.32 | 0.03 | 11% | 0.30 | 0.03 | 11% |
| B | 0.27 | 0.03 | 9% | 0.29 | 0.02 | 8% |
| C | 0.32 | 0.04 | 12% | 0.31 | 0.03 | 11% |
| D | 0.26 | 0.04 | 14% | 0.27 | 0.04 | 14% |
| Average | 0.294 | | | 0.293 | | |
| STDEV | 0.032 | | | 0.016 | | |
| % | 11% | | | 6% | | |

The results of this study include the determination of a value for the coefficient of static friction, $\mu_s$, for skin on standard copy paper. This study used a folded sheet of paper 102c to provide sufficient strength to support the range of weight of the water-filled bucket 102a. The thickness of the folded paper 102c for this pinch strength apparatus 102 was approximately 0.2 cm. The calibrated dynamometer used in the study has a thickness of 2 cm.

4.0 REMOTE EVALUATION OF PINCH STRENGTH

From this study, the value for the coefficient of static friction, $\mu_s$, provides an essential starting point in expanding the potential for remote evaluation of pinch strength. This study determined the coefficient of static friction for skin on copy paper to be 0.29. While it may emerge that the range of values will grow with further testing, it seems likely that the factors affecting individual values can be determined readily and categorized effectively. Most importantly, those factors are less likely to also correlate to injury or disease that may affect pinch strength, allowing use of this technique to serve as valid across changing conditions of concern to patients.

The pinch-bucket method proved reliable in testing pinch strength across a range of weights in order to determine the coefficient of static friction between skin and copy paper. However, use of a specified constant weight for testing pinch strength would be sufficient to determine if an individual suffering from a work-related injury meets or exceeds Maximum Medical Improvement (MMI) criterion and is therefore eligible for medical insurance benefits.

A practical application of this study would be to use a standard sheet of copy paper folded as described herein and wrapped through the handle of a gallon of whole milk (approximately 3.9 kg). This would serve to test a pinch strength of approximately 6.7 kg (3.9/(2×0.29)) using the pinch-bucket method used in this study. The *AMA Guides* specify average thresholds of 4.9 kg for women and 7.5 kg for men. Hence, a gallon of milk could be used to screen an adequate pinch strength threshold for women but is not considered an adequate threshold for men. Alternatively, a 12-pack of cans of water (or soda) for women or an 18-pack for men would meet the AMA Guide threshold.

Figure 4:
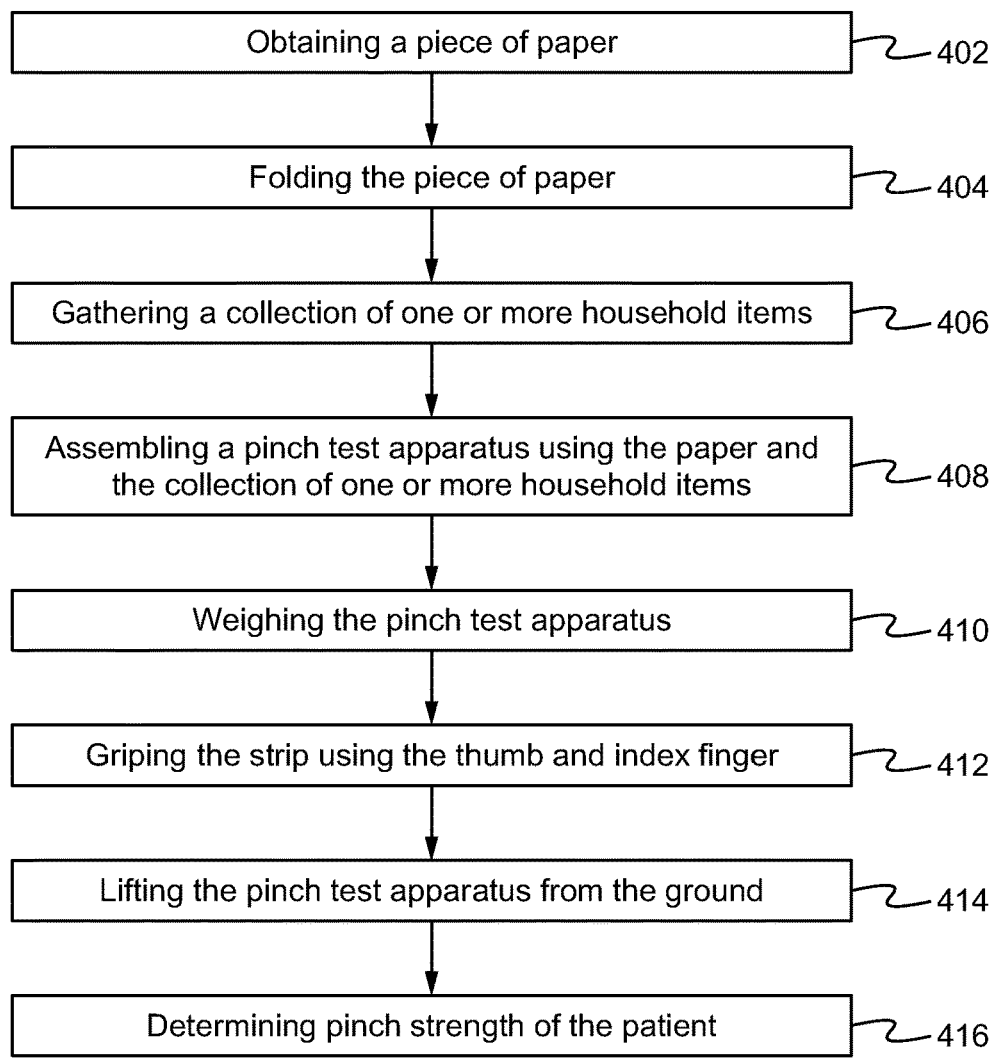
FIG. 4 illustrates a method of testing pinch strength in accordance with some embodiments.

FIG. 4 illustrates a method 400 of testing pinch strength in accordance with some embodiments. The method 400 allows an individual (e.g., practitioner or patient) to determine presence of the normal pinch strength threshold. The method 400 can be performed at home by the patient and remotely evaluated or observed by the practitioner over a network, such the Internet.

At step 402, a piece of paper is obtained. The piece of a paper is an 8.5×11 inches, multipurpose copy printer paper.

At step 404, the piece of paper is folded three time longitudinally to form an eight-ply strip. The thickness of the strip is approximately 0.2 cm.

At step 406, a collection of one or more household items is gathered. An example collection of one or more household items is a gallon of milk. Another example collection of one or more household items is a bucket of water. Yet another example collection of one or more household items is a 12-pack of cans of soda. In an embodiment, the one or more household items in the collection are coupled together and have an "opening" such that the strip can be looped through for lifting up the collection using the folded paper.

In an embodiment, steps 402, 404, and 406 can be performed in any order or concurrently.

At step 408, a pinch test apparatus is assembled using the strip and the collection of one or more household items. In assembling the pinch test apparatus, the strip is looped through the opening of the collection. For example, the opening of the collection can be formed by a handle of the collection (e.g., handle of the milk jug, handle of a bucket, etc.). The ends of the strip are aligned.

At step 410, the pinch test apparatus is weighed. The weight of the pinch test apparatus is relayed to the practitioner. In an embodiment, the weight of the pinch test apparatus is approximately 2.84 kg for women and 4.35 kg for men. Steps 406-410 can be repeated until the pinch test apparatus has the desired weight. For example, more or less water can be added to the bucket at step 406. After the pinch test apparatus has the desired weight, the pinch test apparatus is positioned on the ground.

At step 412, the patient grips the strip using the thumb and index finger. The thumb and index finger are parallel with each other. Prior to step 412, hand skin surfaces can be cleaned to reduce surface skin contaminants.

At step 414, the pinch test apparatus is lifted from the ground by the patient with the arm approximately vertical (with the elbow at full extension), without jerking upward or changing the position of the arm or hand. The lift is remotely observed by the practitioner.

At step 416, pinch strength of the patient is determined. In an embodiment, the pinch strength of the patient is only determined if the practitioner observes that the patient was able to lift the pinch test apparatus properly. Step 414 can be repeated until the practitioner observes that that pinch test apparatus was lifted up properly. The pinch strength ($F_N$) of the patient is determined based on the weight of the pinch test apparatus (mg) determined at step 410 and the previously determined coefficient of static friction between skin and paper ($\mu_s$). Impairment exists if the pinch strength does not meet the pinch strength threshold for the patient (e,g., 4.9 kg for women and 7.5 kg for men).

Using the techniques described herein, an average coefficient of static friction between skin and paper is determined based on pinch-strength measurements and a corresponding maximum weight of bucket and water before slippage occurs, to create a practical application to measure pinch strength. With the coefficient of static friction determined, the pinch-strength threshold for impairment uniquely determines the threshold for a weight of a pinch test apparatus using one or more household material(s), such as bucket and water. A patient using such apparatus at home can therefore put sufficient water in the bucket to reach this weight and see if they can lift the bucket or not, thereby determining whether or not impairment exists.

5.0 OTHER ASPECTS OF DISCLOSURE

Although some of the figures described in the foregoing specification include flow diagrams with steps that are shown in an order, the steps may be performed in any order, and are not limited to the order shown in those flowcharts. Additionally, some steps may be optional, may be performed multiple times, and/or may be performed by different components. All steps, operations and functions of a flow diagram that are described herein are intended to indicate operations that are performed using programming in a special-purpose computer or general-purpose computer, in various embodiments. In other words, each flow diagram in this disclosure, in combination with the related text herein, is a guide, plan or specification of all or part of an algorithm for programming a computer to execute the functions that are described. The level of skill in the field associated with this disclosure is known to be high, and therefore the flow diagrams and related text in this disclosure have been prepared to convey information at a level of sufficiency and detail that is normally expected in the field when skilled persons communicate among themselves with respect to programs, algorithms and their implementation.

In the foregoing specification, the example embodiment(s) of the present invention have been described with reference to numerous specific details. However, the details may vary from implementation to implementation according to the requirements of the particular implement at hand. The example embodiment(s) are, accordingly, to be regarded in an illustrative rather than a restrictive sense.

What is claimed is:

1. A pinch test apparatus comprising:
   a collection of one or more household items coupled together, wherein the collection of one or more household items has an opening; and
   a piece of paper folded longitudinally into a strip, wherein the strip is looped through the opening.

2. The pinch test apparatus of claim 1, wherein the collection of one or more household items includes a bucket of water.

3. The pinch test apparatus of claim 1, wherein the weight of the pinch test apparatus is approximately 2.84 kg or is approximately 4.35 kg.

4. The pinch test apparatus of claim 1, wherein the piece of paper folded is longitudinally three times to form an eight-ply strip.

5. The pinch test apparatus of claim 1, wherein ends of the strip are aligned, and wherein a thickness of the strip is 0.2 cm.

6. The pinch test apparatus of claim 1, further comprising a clothespin coupled with the strip.

7. A method of determining a coefficient of static friction between skin and paper, comprising:
   assembling a pinch strength apparatus,
   wherein the pinch strength apparatus comprises
      a collection of one or more household items coupled together, wherein the collection of one or more household items has an opening, and
      a piece of paper folded longitudinally into a strip,
   wherein assembling the pinch strength apparatus comprises looping the strip through the opening;
   determining a baseline pinch strength;
   determining a threshold weight of the pinch strength apparatus; and
   based on the baseline pinch strength and the weight of the pinch strength apparatus, determining a value of a coefficient of static friction between skin and paper.

8. The method of claim 7, wherein determining the baseline pinch strength comprises using a pinch dynamometer.

9. The method of claim 7, wherein determining the threshold weight of the pinch test apparatus comprises:
   using a hand position in a key pinch to grip the strip;
   lifting the pinch strength apparatus from the ground with elbow at full extension;
   returning the pinch strength apparatus to the ground;
   assessing whether there is slippage of the paper between fingers;
   in response to assessing that there is no slippage,
      increasing mass of the pinch test apparatus and repeating using the hand position in the key pinch, lifting the pinch strength apparatus, returning the pinch strength apparatus, and assessing whether there is slippage;
   in response to assessing that there is slippage, decreasing the mass of the pinch test apparatus and repeating using the hand position in the key pinch, lifting the pinch strength apparatus, returning the pinch strength apparatus, and assessing whether there is slippage; and
   determining the mass of the pinch test apparatus.

10. The method of claim 7, wherein the key pinch involves a volar pad of a thumb on one side of an object and a radial side of a distal phalanx of an index finger on an opposite side of the object.

11. The method of claim 7, wherein a thickness of the strip is 0.2 cm.

12. The method of claim 7, wherein the pinch strength apparatus further comprises a clothespin, wherein the clothespin is coupled horizontally to the strip and is configured as a guide for positioning fingers in the hand position.

13. The method of claim 7, wherein the collection one or more household items includes a bucket of water.

14. A method of testing a pinch strength, comprising:
   assembling a pinch strength apparatus,
   wherein the pinch strength apparatus comprises
      a collection of one or more household items coupled together, wherein the collection of one or more household items has an opening, and
      a piece of paper folded longitudinally into a strip,
   wherein assembling the pinch strength apparatus comprises looping the strip through the opening;
   using a hand position in a key pinch to grip the strip; and
   lifting the pinch strength apparatus from the ground.

15. The method of claim 14, wherein the collection one or more household items includes a bucket of water.

16. The method of claim 14, wherein the weight of the pinch test apparatus is approximately 2.84 kg or is approximately 4.35 kg, and further comprising:
   assessing whether there is slippage of the paper between fingers when the pinch strength apparatus is lifted from the ground; and
   determining whether an impairment exists based on at least the assessment.

17. The method of claim 14, wherein the piece of paper folded is longitudinally three times, wherein a thickness of the strip is 0.2 cm.

18. The method of claim 14, wherein the key pinch involves a volar pad of a thumb on one side of an object and a radial side of a distal phalanx of an index finger on an opposite side of the object.

19. The method of claim 14, wherein assembling, using and lifting are supervised via telemedicine.

20. The method of claim 14, further comprising:
   determining a weight of the pinch test apparatus; and
   based on the weight of the pinch test apparatus and a coefficient of static friction between skin and paper, determining pinch strength determining the pinch strength comprises.

* * * * *